United States Patent
Taylor et al.

(10) Patent No.: US 9,370,505 B2
(45) Date of Patent: Jun. 21, 2016

(54) PHARMACEUTICAL COMPOSITIONS COMPRISING AN AROMATSE INHIBITORS

(75) Inventors: Ann Taylor, Wickford, RI (US); Lloyd B. Klickstein, Newton, MA (US); Jeewan Thakur, Basel (CH)

(73) Assignee: Mereo BioPharma 2 Limited, London (GB)

( * ) Notice: Subject to any disclaimer, the term of this patent is extended or adjusted under 35 U.S.C. 154(b) by 0 days.

(21) Appl. No.: 14/342,813

(22) PCT Filed: Sep. 6, 2012

(86) PCT No.: PCT/US2012/053846
§ 371 (c)(1),
(2), (4) Date: Mar. 5, 2014

(87) PCT Pub. No.: WO2013/036563
PCT Pub. Date: Mar. 14, 2013

(65) Prior Publication Data
US 2014/0213622 A1 Jul. 31, 2014

Related U.S. Application Data

(60) Provisional application No. 61/532,459, filed on Sep. 8, 2011, provisional application No. 61/638,588, filed on Apr. 26, 2012.

(51) Int. Cl.
*A61K 31/4196* (2006.01)
*A61K 9/48* (2006.01)

(52) U.S. Cl.
CPC .............. *A61K 31/4196* (2013.01); *A61K 9/485* (2013.01); *A61K 9/4833* (2013.01); *A61K 9/4858* (2013.01); *A61K 9/4866* (2013.01)

(58) Field of Classification Search
CPC ................................................. A61K 31/4196
See application file for complete search history.

(56) References Cited

U.S. PATENT DOCUMENTS 5,637,605 A * 6/1997 Lang et al. ............... 514/383

FOREIGN PATENT DOCUMENTS

EP  0490816A2 A2  6/1992
WO  03/082254 A1  9/2003

OTHER PUBLICATIONS

Jonat S, Hasenzahl S, Gray A, Schmidt PC. Mechanism of glidants: investigation of the effect of different colloidal silicon dioxide types on powder flow by atomic force and scanning electron microscopy. J Pharm Sci. Oct. 2004;93(10):2635-44.*
nBent.com. "Sodium Starch Glycolate". Feb. 2004.*
De Boer, H et al: "Letrozole normalizes serum testosterone in severely obese men with hypogonadotropic hypogonadism", Diabetes, Obesity and Metabolism, vol. 7, No. 3 pp. 211-215.
Lang, M et al: "Structure-activity relationships and binding model of novel aromatase inhibitorS", Journal of Steroid Biochemistry and Molecular Biology, vol. 44, No. 4-6, pp. 421-428, 1993.

* cited by examiner

*Primary Examiner* — Paul Zarek
(74) *Attorney, Agent, or Firm* — Wolff IP, A Prof. Corp.; Jessica Wolff

(57) ABSTRACT

The invention relates to low-dose pharmaceutical compositions comprising the aromatase inhibitor 4,4'-[fluoro-(1-H-1, 2,4-triazol-1-yl)methylene]bisbenzonitrile, as the active ingredient in a suitable carrier. The present invention also relates to a process for their preparation and to their use as therapeutic agents.

17 Claims, No Drawings

PHARMACEUTICAL COMPOSITIONS COMPRISING AN AROMATSE INHIBITORS

FIELD OF THE INVENTION

The present invention relates to low-dose pharmaceutical compositions comprising the aromatase inhibitor 4,4'-[fluoro-(1-H-1,2,4-triazol-1-yl)methylene]bisbenzonitrile, as the active ingredient in a suitable carrier. The present invention also relates to a process for their preparation and to their use as medicaments.

BACKGROUND OF THE INVENTION

The aromatase inhibitor 4,4'-[fluoro-(1-H-1,2,4-triazol-1-yl)methylene]bisbenzonitrile, also known as 4-[α-4-Cyanophenyl)-α-fluoro-1-(1,2,4-triazolyl)methyl]-benzonitrile or CGP47645, first described in 1992 [EP 490 816 and U.S. Pat. No. 5,637,605], has the following structural formula (I)

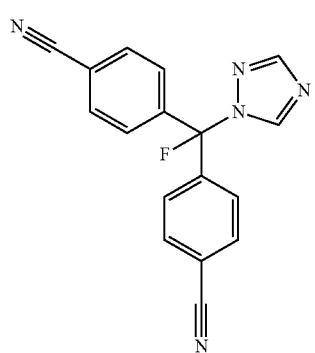

(I)

The compound 4,4'-[fluoro-(1-H-1,2,4-triazol-1-yl)methylene]bisbenzonitrile is a crystalline compound with a sharp melting endotherm at 169.5° C. The crystalline powder is not hygroscopic and is poorly soluble in water.

4,4'-[fluoro-(1-H-1,2,4-triazol-1-yl)methylene]bisbenzonitrile (CGP47645) is a highly specific and potent aromatase inhibitor which was shown here within to have a longer half life in humans than does letrozole (Femara®), a marketed aromatase inhibitor to which CGP47645 is structurally related. In vitro experiments with human placental microsomal aromatase demonstrated an $IC_{50}$=6 nM. Oral administration of CGP47645 to rats demonstrated a T½ of 75 hours. The exposure expressed as AUC was proportional to the administered dose. In two different aromatase dependent experimental models, inhibition of androstenedione-induced uterine hypertrophy in rats and inhibition of DMBA-induced mammary tumors in rats, the $ED_{50}$ was 0.003 mg/kg and 0.01 mg/kg, respectively. These results suggested CGP47645 is approximately 10-fold more potent than letrozole.

4,4'-[fluoro-(1-H-1,2,4-triazol-1-yl)methylene]bisbenzonitrile is a highly potent and cohesive drug which needs to be dispensed in low doses. Such drugs require a careful formulation and production in order to produce solid oral dosage forms with acceptable content uniformity and physical stability. There is a need to formulate 4,4'-[fluoro-(1-H-1,2,4-triazol-1-yl)methylene]bisbenzonitrile into pharmaceutical compositions, especially solid oral dosage forms, such that the therapeutic benefits of the compound may be delivered safely to a patient in need thereof.

Formulation of low dose medicines can be very challenging and problems related to content uniformity and physical stability may arise. Content uniformity is a key parameter for oral solid dosage forms, because significant deviations in active content may impact the performance of the product in terms of efficacy and safety. The selection of the excipients and the specific steps during the manufacturing are critical factors and need to be controlled in order to get a homogenous and segregation-free low dose formulation.

Accordingly, the present invention provides a solid pharmaceutical composition suitable for oral administration, comprising CGP47645.

SUMMARY OF THE INVENTION

In one aspect, the present invention is directed to a low-dose pharmaceutical composition, preferably in form of a capsule, comprising a blended mixture comprising
 (a) a therapeutically effective amount of 4,4'-[fluoro-(1-H-1,2,4-triazol-1-yl)methylene]bisbenzonitrile;
 (b) a filler or a mixture of one or more, e.g. 1, 2, or 3, fillers;
 (c) a disintegrant or a mixture of one or more, e.g. 1, 2 or 3 disintegrants;
 (d) a lubricant or a mixture of one or more, e.g. 1, 2 or 3 lubricants, and
 (e) a glidant or a mixture of one or more, e.g. 1, 2 or 3 glidants.

In another aspect, the present invention is directed to a method for preparing a pharmaceutical composition according to the present invention comprising the steps of:
 (a) sequentially adding two portions of a filler or a mixture of fillers and one portion of the therapeutic compound 4,4'-[fluoro-(1-H-1,2,4-triazol-1-yl)methylene]bisbenzonitrile (CGP47645) in the order first portion filler, therapeutic compound, second portion filler into a suitable mixing vessel and mixing the layers of the components using a suitable mixer to produce a pre-mix,
 (b) sieving the pre-mix through a sieve with a mesh size of not more than 1.0 mm, preferably a mesh size of 0.5 mm,
 (c) optionally mixing the sieved pre-mix using a suitable mixer,
 (d) sieving a mixture of the remaining excipients, except the lubricant, through a sieve with a mesh size of not more than 1.0 mm, preferably a mesh size of 0.5 mm,
 (e) mixing the pre-mix with the mixture of the remaining excipients, except the lubricant, using a suitable mixer,
 (f) sieving the resulting mixture through a sieve with a mesh size of not more than 1.0 mm, preferably a mesh size of 0.5 mm,
 (g) optionally mixing the sieved mixture using a suitable mixer,
 (h) sieving the lubricant, through a sieve with a mesh size of not more than 1.0 mm, preferably a mesh size of 0.5 mm and subsequently adding the lubricant to the resulting mixture of step (f) or (g),
 (i) mixing the resulting mixture using a suitable mixer to obtain the final blend,
 (j) filling the final blend of step (i) into capsules, optionally using a suitable capsule filling machine.

In a further aspect, the present invention provides the pharmaceutical compositions according the present invention for use in the treatment or prevention of a condition or disorder associated with aromatase activity, including, but not limited to estrogen dependent diseases, such as breast tumor, endometriosis, uterine fibroids, uterine leiomyoma, uterine adenomyosis, dysfunctional uterine bleeding and abnormal endometrial thickening; premature labour; endometrial tumors in women; or gynaecomastia in men.

In one embodiment the present invention is directed to the pharmaceutical compositions according to the present invention for use in the treatment of a male patient in need of increased testosterone levels, preferably an overweight or obese male patient in need of increased testosterone levels.

In another embodiment the present invention is directed to the pharmaceutical compositions according to the present invention for use in the treatment of hypogonadism or hypogonadotropic hypogonadism in a male patient, preferably an overweight or obese male patient.

DETAILED DESCRIPTION OF THE INVENTION

There are provided novel pharmaceutical compositions that comprise 4,4'-[fluoro-(1-H-1,2,4-triazol-1-yl)methylene]bisbenzonitrile (CGP47645). The pharmaceutical compositions are in the form of solid oral dosage forms, especially capsules with an immediate release profile. The pharmaceutical compositions may be prepared by preparing a blended mixture comprising 4,4'-[fluoro-(1-H-1,2,4-triazol-1-yl)methylene]bisbenzonitrile (CGP47645) and pharmaceutically acceptable excipients, wherein said blended mixture subsequently is filled into capsules e.g. by using an encapsulating machinery.

Any capsules as known in the art may be used to encapsulate the blended mixture. An example of such a capsule are hard gelatin capsules, for example CONI-SNAP manufactured by Capsugel of Morris Plains, N.J. Suitable sizes for such capsules include, but are not limited to sizes Nos. 0 through 5.

Pharmaceutical compositions, in particular in the form of capsules, according to the present invention may contain, for example, from about 0.01 mg to up to 20 mg, preferably from about 0.01 mg to about 10 mg, most preferably from about 0.01 to about 5 mg of the therapeutic compound per capsule; e.g. about 0.01 mg, about 0.05 mg, about 0.1 mg, about 0.3 mg, about 0.5 mg, about 1 mg, about 2 mg, about 3 mg, about 5 mg, about 10 mg or about 20 mg therapeutic compound per capsule.

As used herein, the term "therapeutic compound" refers to 4,4'-[fluoro-(1-H-1,2,4-triazol-1-yl)methylene]bisbenzonitrile (CGP47645) of formula I:

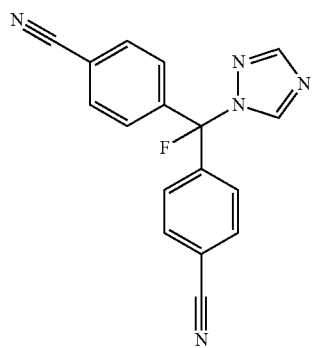

(I)

As used herein the term "pharmaceutical composition" means, for example, a mixture containing a specified amount of a therapeutic compound, e.g. a therapeutically effective amount, in a pharmaceutically acceptable carrier to be administered to a mammal, e.g., a human in order to treat a disease.

As used herein the term "pharmaceutically acceptable" refers to those compounds, materials, compositions and/or dosage forms, which are, within the scope of sound medical judgment, suitable for contact with the tissues of mammals, especially humans, without excessive toxicity, irritation, allergic response and other problem complications commensurate with a reasonable benefit/risk ratio.

As used herein the term "immediate-release" refers to the rapid release of the majority of the therapeutic compound, e.g., greater than about 50%, about 55%, about 60%, about 65%, about 70%, about 75%, about 80%, or about 90% within a relatively short time, e.g., within 1 hour, 40 minutes, 30 minutes or 20 minutes after oral ingestion. Particularly useful conditions for immediate-release are release of at least or equal to about 80% of the therapeutic compound within thirty minutes after oral ingestion. The particular immediate-release conditions for a specific therapeutic compound will be recognized or known by one of ordinary skill in the art. The immediate release profile can be determined from an in vitro dissolution test.

As used herein the term "excipient" refers to a pharmaceutically acceptable ingredient that is commonly used in the pharmaceutical technology for preparing solid oral dosage formulations. Examples of categories of excipients include, but are not limited to, binders, disintegrants, lubricants, glidants, stabilizers, fillers and diluents. The amount of each excipient used may vary within ranges conventional in the art. The following references which are all hereby incorporated by reference disclose techniques and excipients used to formulate oral dosage forms. See The Handbook of Pharmaceutical Excipients, 4th edition, Rowe et al., Eds., American Pharmaceuticals Association (2003); and Remington: the Science and Practice of Pharmacy, 20th edition, Gennaro, Ed., Lippincott Williams & Wilkins (2000).

The term "prevention" refers to prophylactic administration to a healthy subject to prevent the development of a condition. Moreover, the term "prevention" means prophylactic administration to patients being in a pre-stage of a condition to be treated.

The term "treatment" is understood the management and care of a patient for the purpose of combating a disease, condition or disorder.

The present invention provides a low-dose pharmaceutical composition, preferably in form of a capsule, comprising a blended mixture comprising
(a) a therapeutically effective amount of 4,4'-[fluoro-(1-H-1,2,4-triazol-1-yl)methylene]bisbenzonitrile;
(b) a filler or a mixture of one or more, e.g. 1, 2, or 3 fillers;
(c) a disintegrant or a mixture of one or more, e.g. 1, 2 or 3 disintegrants;
(d) a lubricant or a mixture of one or more, e.g. 1, 2 or 3 lubricants, and
(e) a glidant or a mixture of one or more, e.g. 1, 2 or 3 glidants.

A therapeutically effective amount of 4,4'-[fluoro-(1-H-1,2,4-triazol-1-yl)methylene]bisbenzonitrile may be for example from about 0.01 mg to up to 20 mg, preferably from about 0.01 mg to about 10 mg, most preferably from about 0.01 to about 5 mg per capsule; e.g. about 0.01 mg, about 0.05 mg, about 0.1 mg, about 0.3 mg, about 0.5 mg, about 1 mg, about 2 mg, about 3 mg, about 5 mg, about 10 mg or about 20 mg per capsule.

In one embodiment, the pharmaceutical composition, in particular in the form of capsules, according to the present invention contains from about 0.1 mg to about 10 mg of the therapeutic compound per capsule, preferably from about 0.1 mg to about 5 mg of the therapeutic compound per capsule.

The fillers to be employed in accordance with the present invention include, without limitation, microcrystalline cellulose (e.g., cellulose MK GR and products available under the registered trade marks AVICEL, FILTRAK, HEWETEN or PHARMACEL, Vivapur, emcocel, tabulose); low-substituted hydroxypropyl cellulose; hydroxyethyl cellulose; hydroxypropyl methyl cellulose; carbohydrates, such as sugars, sugar alcohols, starches or starch derivatives, for example sucrose, lactose, dextrose, saccharose, glucose, sorbitol, mannitol, xylitol, potato starch, maize starch, rice starch, wheat starch or amylopectin; tricalcium phosphate; calcium hydrogen phosphate; calcium sulfate; dibasic calcium phosphates; magnesium oxide or mixtures thereof.

In some embodiments the filler suitable for use in accordance with the present invention has disintegrant properties. Fillers with disintegrant properties include, without limitation, maize starch, microcrystalline cellulose, alginic acid and pregelatinized starch or mixtures thereof.

Preferably the filler is selected from the group consisting of microcrystalline cellulose, lactose, maize starch and mixtures thereof.

Preferably the lactose is lactose monohydrate. In some embodiments said lactose monohydrate is spray dried.

More preferably the filler is a mixture of lactose monohydrate, microcrystalline cellulose and maize starch.

The filler may be employed in an amount ranging from about 50% to about 99%, preferably from about 70% to about 97%, most preferably from about 80-96%, e.g, 85-95% or 89-94% by weight of the capsule content.

In one embodiment, the filler is a combination of lactose monohydrate and two other fillers, e.g. microcrystalline cellulose and maize starch. In one aspect of this embodiment the filler is a mixture of lactose monohydrate, microcrystalline cellulose and maize starch, wherein the amount of lactose monohydrate in said mixture is between about 60% and about 75% by weight of the mixture of fillers, preferably between about 65% and 70% by weight of the mixture of fillers; the amount of microcrystalline cellulose in said mixture is between about 10% and about 30% by weight of the mixture of fillers, preferably between about 15% and about 25% by weight of the mixture of fillers; the amount of maize starch in said mixture is between about 5% and about 20% by weight of the mixture of fillers, preferably between about 7.5% and about 17.5% by weight of the mixture of fillers.

Examples of disintegrants to be employed in accordance with the present invention include, without limitation, carboxymethylcellulose calcium (CMC-Ca), carboxymethylcellulose sodium (CMC-Na) or crosscarmellose sodium, e.g. AC-DI-SOL, Sodium Starch Glycolate (SSG), alginic acid, sodium alginate and guar gum or mixtures thereof; preferably crosscarmellose sodium, e.g. AC-DI-SOL, cross-linked polyvinyl pyrrolidone (e.g. CROSPOVIDONE, POLYPLASDONE or KOLLIDON XL) and Sodium Starch Glycolate (SSG) or mixtures thereof.

A preferred disintegrant is Sodium Starch Glycolate (SSG).

The disintegrant may be employed in an amount ranging from about 1% to about 10%, preferably from about 2% to about 7.5%, most preferably from about 3% to about 6%, by weight of the capsule content.

The lubricants to be employed in accordance with the present invention include, without limitation, magnesium stearate, aluminum or calcium silicate, stearic acid, cutina, PEG 4000-8000, talc or mixtures thereof, preferably sodium stearyl fumarate or magnesium stearate, more preferably magnesium stearate.

The lubricant may be employed in an amount ranging from about 0.1% to about 10%, preferably from about 0.25% to about 5%, e.g. about 0.5% to about 2%, by weight of the capsule content.

Suitable glidants than can be used in accordance with the present invention include, without limitation, colloidal silicon dioxide (e.g., Aerosil 200), magnesium trisilicate, powdered cellulose, starch, talc or mixtures thereof, preferably colloidal silicon dioxide.

The glidant may be employed in an amount ranging from about 0.05% to about 5%, preferably from about 0.1% to about 1%, more preferably from about 0.25% to about 1%, e.g. 0.25%, 0.5% or 0.75%, by weight of the capsule content.

In one embodiment of the present invention the blended mixture which may be filled into the capsule comprises
(a) a therapeutically effective amount of 4,4'-[fluoro-(1-H-1,2,4-triazol-1-yl)methylene]bisbenzonitrile,
(b) a mixture of 3 fillers, wherein said fillers are microcrystalline cellulose, lactose monohydrate and maize starch,
(c) a disintegrant, wherein said disintegrant is Sodium Starch Glycollate (SSG),
(d) a lubricant, wherein said lubricant is magnesium stearate,
(e) a glidant, wherein said glidant is colloidal silicon dioxide (e.g., Aerosil 200).

In a particular preferred embodiment the blended mixture which may be filled into the capsule comprises
(a) a therapeutically effective amount of 4,4'-[fluoro-(1-H-1,2,4-triazol-1-yl)methylene]bisbenzonitrile,
(b) a mixture of 3 fillers, wherein said fillers are microcrystalline cellulose, lactose monohydrate and maize starch,
(c) a disintegrant, wherein said disintegrant is Sodium Starch Glycollate (SSG),
(d) a lubricant, wherein said lubricant is magnesium stearate,
(e) a glidant, wherein said glidant is colloidal silicon dioxide (e.g., Aerosil 200),
wherein said therapeutically effective amount of 4,4'-[fluoro-(1-H-1,2,4-triazol-1-yl)methylene]bisbenzonitrile is from about 0.01 mg to up to 20 mg, preferably from about 0.01 mg to about 10 mg, most preferably from about 0.01 mg to about 5 mg per capsule; e.g. about 0.01 mg, about 0.05 mg, about 0.1 mg, about 0.3 mg, about 0.5 mg, about 1 mg, about 2 mg, about 3 mg, about 5 mg, about 10 mg or about 20 mg per capsule;
said mixture of fillers is employed in an amount ranging from about 50% to about 99%, preferably from about 70% to about 97%, most preferably from about 80% to to about 96%, e.g, 85-95% or 89-94%, by weight of the capsule content;
said disintegrant is employed in an amount ranging from about 1% to about 10%, preferably from about 2% to about 7.5%, most preferably from about 3% to about 6%, e.g. 4% or 5%, by weight of the capsule content;
said lubricant is employed in an amount ranging from about 0.1% to about 10%, preferably from about 0.25% to about 5%, e.g. 0.5%, 1% or 2%, by weight of the capsule content and
said glidant is employed in an amount ranging from about 0.05% to about 5%, preferably from about 0.1% to about 1%, more preferably from about 0.25% to about 1%, e.g. 0.25%, 0.5% or 0.75%, by weight of the capsule content.

Another aspect of the present invention relates to a method for preparation a low-dose capsule formulation of 4,4'-[fluoro-(1-H-1,2,4-triazol-1-yl)methylene]bisbenzonitrile (CGP47645).

Accordingly there is also provided a method for preparing a low-dose pharmaceutical composition, in the form of a capsule, as described herein above comprising the steps of:

(a) sequentially adding two portions of a filler or a mixture of fillers and one portion of the therapeutic compound 4,4'-[fluoro-(1-H-1,2,4-triazol-1-yl)methylene]bisbenzonitrile (CGP47645) in the order first portion filler, therapeutic compound, second portion filler into a suitable mixing vessel and mixing the layers of the components using a suitable mixer to produce a pre-mix;

(b) sieving the pre-mix through a sieve with a mesh size of not more than 1.0 mm, preferably a mesh size of 0.5 mm;

(c) optionally mixing the sieved pre-mix using a suitable mixer;

(d) sieving a mixture of the remaining excipients, except the lubricant, through a sieve with a mesh size of not more than 1.0 mm, preferably a mesh size of 0.5 mm;

(e) mixing the pre-mix with the mixture of the remaining excipients, except the lubricant, using a suitable mixer;

(f) sieving the resulting mixture through a sieve with a mesh size of not more than 1.0 mm, preferably a mesh size of 0.5 mm;

(g) optionally mixing the sieved mixture using a suitable mixer;

(h) sieving the lubricant, through a sieve with a mesh size of not more than 1.0 mm, preferably a mesh size of 0.5 mm and subsequently adding the lubricant to the resulting mixture of step (f) or (g);

(i) mixing the resulting mixture using a suitable mixer to obtain the final blend;

(j) filling the final blend of step (i) into capsules, optionally using a suitable capsule filling machine;

In one embodiment of the present invention the filler used for the pre-mix is maize starch or lactose monohydrate or a mixture thereof, preferably maize starch.

In one embodiment the whole amount of maize starch or lactose monohydrate is used for the pre-mix. In another embodiment only a part of the maize starch or the lactose monohydrate is used for the premix.

Preferably the filler for the pre-mix is maize starch and the amount of maize starch in the pre-mix is between about 5% to about 100% by weight of the total amount of maize starch in the blend, such as for example about 13%, about 70% or about 100% by weight of the total amount of maize starch in the blend.

In one embodiment of the present invention the two portions of filler in step (a) are used in a ratio of about 1:1.

In another embodiment steps (c) and/or (g) are mandatory steps.

As mentioned above, formulation of low dose medicines can be very challenging and problems related to content uniformity and physical stability may arise. Content uniformity is a key parameter for oral solid dosage forms, because significant deviations in active content may impact the performance of the product in terms of efficacy and safety. The selection of the excipients and the specific steps during the manufacturing are critical factors and need to be controlled in order to get a homogenous and segregation-free low dose formulation.

It has been found that the blend uniformity of the final blended mixture of the low-dose capsule formulations of 4,4'-[fluoro-(1-H-1,2,4-triazol-1-yl)methylene]bisbenzonitrile (CGP47645) of the present invention is between 95% and 101% versus the theoretical amount. Similarly, the content uniformity after the filling of the blend into the capsules is between 97% and 104% versus the label. No trend towards segregation was observed (Example 3).

Accordingly, in one embodiment of the invention the blend uniformity of the low dose capsule formulation of 4,4'-[fluoro-(1-H-1,2,4-triazol-1-yl)methylene]bisbenzonitrile (CGP47645) as described herein above is of between 90% and 110%, preferably of between 95% and 105% versus the theoretical amount.

In another embodiment of the invention the content uniformity of the low dose capsule formulation of 4,4'-[fluoro-(1-H-1,2,4-triazol-1-yl)methylene]bisbenzonitrile (CGP47645) as described herein above is of between 90% and 110%, preferably of between 95% and 105% versus the theoretical amount.

In humans, the compound 4,4'-[fluoro-(1-H-1,2,4-triazol-1-yl)methylene]bisbenzonitrile (CGP47645) formulated in the pharmaceutical composition according to the present invention was initially studied in a single, ascending dose protocol in human female volunteers to assess safety and tolerability and pharmacokinetic (PK) and pharmacodynamic (PD) effects of single doses of CGP47645 (see Example 4).

The study showed that the median $T_{max}$ occurred within 1 hour of ingestion, and that the half life was extremely long, approximately 25 days at doses above 0.01 mg.

In one aspect the invention relates to the pharmaceutical compositions as described herein above for use in the treatment or prevention of a condition or disorder associated with aromatase activity, including, but not limited to estrogen dependent diseases, such as breast tumor, endometriosis, uterine fibroids, uterine leiomyoma, uterine adenomyosis, dysfunctional uterine bleeding and abnormal endometrial thickening; premature labour; endometrial tumors in women; or gynaecomastia in men.

In one embodiment the invention relates to the pharmaceutical compositions as described herein above for use in the treatment of a male patient in need of increased testosterone levels, preferably an overweight or obese male patient in need of increased testosterone levels.

In another embodiment the invention relates to the pharmaceutical compositions as described herein above for use in the treatment of hypogonadism or hypogonadotropic hypogonadism in a male patient, preferably an overweight or obese male patient.

In another aspect the invention provides a method for treating or preventing a condition or disorder associated with aromatase activity, including but not limited to estrogen dependent diseases, such as breast tumor, endometriosis, uterine fibroids, uterine leiomyoma, uterine adenomyosis, dysfunctional uterine bleeding and abnormal endometrial thickening; premature labour; endometrial tumors in women; or gynaecomastia in men, comprising administering to an animal, including a human patient, in need of such treatment a therapeutically effective amount of the pharmaceutical composition according to the present invention.

In one embodiment the invention relates to a method for the treatment of a male patient in need of increased testosterone levels, preferably an overweight or obese male patient in need of increased testosterone levels, comprising administering to said patient a therapeutically effective amount of the pharmaceutical composition as described herein above.

In another embodiment the invention relates to a method for the treatment of hypogonadism or hypogonadotropic hypogonadism in a male patient, preferably an overweight or obese male patient, comprising administering to said patient a therapeutically effective amount of the pharmaceutical composition as described herein above.

The present invention likewise provides the use of a pharmaceutical composition according to the present invention for the manufacturing of a medicament for the treatment or prevention of a condition or disorder associated with aromatase activity, including, but not limited to estrogen dependent diseases, such as breast tumor, endometriosis, uterine fibroids, uterine leiomyoma, uterine adenomyosis, dysfunctional uterine bleeding and abnormal endometrial thickening; premature labour; endometrial tumors in women; or gynaecomastia in men.

In one embodiment the invention relates to the use of a pharmaceutical composition as described herein above for the manufacturing of a medicament for the treatment of a male patient in need of increased testosterone levels, preferably an overweight or obese male patient in need of increased testosterone levels.

In another embodiment the invention relates to the use of a pharmaceutical composition as described herein above for the manufacturing of a medicament for the treatment of hypogonadism or hypogonadotropic hypogonadism in a male patient, preferably an overweight or obese male patient.

The following examples are illustrative, but do not serve to limit the scope of the invention described herein. The examples are meant only to suggest a method of practicing the present invention.

EXAMPLES

Example 1

Preparation of 4,4'-[fluoro-(1-H-1,2,4-triazol-1-yl)methylene]bisbenzonitrile

The following example describes a method for the synthesis of 4,4'-[fluoro-(1-H-1,2,4-triazol-1-yl)methylene]bisbenzonitrile (also known as 4-[α-4-Cyanophenyl)-α-fluoro-1-1,2,4-triazolyl)-methyl]-benzonitrile or CGP47645) as disclosed within Lang et al., U.S. Pat. No. 5,637,605:

A solution of 0.8 mmol of potassium hexamethyldisilazane in 1.6 ml of toluene is diluted with 5 ml of THF and, after cooling to −78° C., a solution of 190 mg of 4-[α-(4-cyanophenyl)-1-(1,2,4-triazolyl)methyl]-benzonitrile (see EP-A-236 940, Ex. 20a) in 3 ml of THF is added thereto. After stirring for 1 hour at the same temperature, there are added dropwise to the dark-red solution 301 mg of N-fluoro-dimethylsaccharinsultam in 3 ml of THF. After a further 1.5 hours at −78° C., the reaction mixture is heated to room temperature within 1 hour and poured onto a saturated solution of ammonium chloride in water and then extracted with methylene chloride. Drying over magnesium chloride and concentration of the solvent by evaporation yields the crude product which is purified by means of flash-chromatography ($SiO_2$, hexane/ethyl acetate 9:1, 4:1 to 1:1). TLC ($SiO_2$, $CHCl_3$/methanol 9:1, Rf=0.85); IR (KBr): 2220 $cm^{-1}$; $^1$H-NMR ($CDCl_3$): δ (ppm)=7.46 and 7.76 (8H, m), 8.07 (1H,$), 8.16 (1H,$).

All disclosure relevant to the preparation of 4-[α-4-Cyanophenyl)-α-fluoro-1-1,2,4-triazolyl)-methyl]-benzonitrile described in Lang et al., U.S. Pat. No. 5,376,669 is hereby incorporated by reference herein.

The above paragraph refers to EP-A-236 940, Ex. 20a. The U.S. equivalent to EP-236 940 is Bowman, U.S. Pat. No. 4,749,713. Example 20 (a) of EP-A-236 940 (U.S. equivalent U.S. Pat. No. 4,749,713) states that 4-[1-(1,2,4-Triazolyl)-methyl]-benzonitrile is reacted with potassium tert-butoxide and 4-fluorobenzonitrile according to the procedure in Example 2 of U.S. Pat. No. 4,749,713 to yield 4[α-(4-cyanophenyl)-1-(1,2,4-triazolyl)-methyl]benzonitrile, m.p. 181° C.-183° C.

The procedure of Example 2 of U.S. Pat. No. 4,749,713 provides that: A suspension of potassium tert-butoxide (61.6 g) in dimethylformamide (500 mL) is stirred and cooled to −10° C. (ice-salt bath), and a solution of 4-(1-imidazolylmethyl)-benzonitrile (45.6 g) in dimethylformamide (250 mL) is added so that the reaction temperature remains below 0° C.

The resulting solution is stirred at 0° C. for 0.5 hour and then a solution of 4-fluorobenzonitrile (38.3 g) in dimethylformamide (100 mL) is added while keeping reaction temperature below 5° C. After 0.75 hour, the reaction mixture is neutralized to pH 7 by addition of sufficient 3N hydrochloric acid and the bulk of the solvents are then removed under reduced pressure. The residue is diluted with water (500 mL) and the crude product is extracted into ethyl acetate (3×200 mL). The combined extracts are then extracted with 3N hydrochloric acid (3×150 mL) and, after washing the latter acid extracts with ethyl acetate (100 mL), the solution is made basic (pH 8) with 6N ammonium hydroxide and the product is again extracted into ethyl acetate (3×150 mL). The combined extracts are dried ($MgSO4$), decolorized by treatment with charcoal, and then evaporated to give crude 4-[α-(4-cyanophenyl)-1-imidazolylmethyl]-benzonitrile as an oil. This material is dissolved in isopropanol (250 mL) and the warm solution is stirred with succinic acid (14.4 g). Upon dilution with diethyl ether (100 mL) and stirring at ambient temperature, the hemi-succinate salt separates. The salt is filtered off, washed with a little cold isopropanol and then air dried to afford 4-[α-(4-cyanophenyl)-1-imidazolylmethyl]-benzonitrile hemisuccinate, m.p. 149° C.-150° C. The hemifumarate salt has m.p. 157° C.-158° C.

All disclosure relevant to the preparation of 4[α-(4-cyanophenyl)-1-(1,2,4-triazolyl)-methyl]benzonitrile described in Bowman, U.S. Pat. No. 4,749,713 is hereby incorporated by reference herein.

Example 2

Low-Dose Capsule Formulations of 4,4'-[fluoro-(1-H-1,2,4-triazol-1-yl)methylene]bisbenzonitrile (CGP47645)

CGP47645 containing hard gelatine capsules are prepared by the following process: The required excipients, in the respective amounts to yield the final composition as indicated in Table 1 below, and the appropriate amount of CGP47645 drug substance are weighed.

Then, approximately 50% of corn starch is filled into suitable container, the drug substance is added, followed by the remaining 50% of corn starch to get a sandwich of drug substance between two layers of maize starch. Blending and sieving this mixture yields the drug substance (DS) premix.

The remaining excipients (microcrystalline cellulose, spray-dried lactose, sodium starch glycolate, and colloidal silicon dioxide [Aerosil® 200]) are mixed and sieved and transfer into a suitable container. Then the DS premix is added into container containing the sieved excipients and the mixture is blended together. Finally, pre-sieved Magnesium stearate is added to the blend containing the DS and this mixture is blended again to yield the final blend. The final blend is filled into hard gelatin capsules.

All the excipients comply with the requirements of the applicable compendial monographs (Ph.Eur., NF). The hard gelatine capsules are packaged in HDPE bottles with aluminum induction seal equipped with child-resistant screw-cap closures.

The final dosage form is a hard gelatine capsule containing a white to yellowish powder in a pink opaque capsule, size 1 or 3.

The following Table 1 indicates the composition of the CGP47645 hard gelatin capsule of 0.1 mg, 0.5, 1 mg and 10 mg strength.

TABLE 1

| Ingredient | Amount per capsule (mg) | | | | |
| --- | --- | --- | --- | --- | --- |
| | 0.1 mg[1] | 0.1 mg[2] | 0.5 mg[1] | 1 mg[2] | 10 mg[2] |
| Capsule content | | | | | |
| CGP47645 | 0.1 | 0.1 | 0.5 | 1.0 | 10.0 |
| Lactose monohydrate | 96.0 | 192.0 | 96.0 | 192.0 | 175.5 |
| Cellulose, microcrystalline | 30.0 | 60.0 | 30.0 | 60.0 | 50.0 |
| Corn Starch | 14.15 | 28.4 | 13.75 | 27.5 | 40.0 |
| Sodium starch glycolate (Type A) | 7.5 | 15.0 | 7.5 | 15.0 | 15.0 |
| Magnesium Stearate | 1.5 | 3.0 | 1.5 | 3.0 | 3.0 |
| Silica, colloidal anhydrous | 0.75 | 1.5 | 0.75 | 1.5 | 1.5 |
| Capsule fill weight | 150.0 | 300.0 | 150 | 300.0 | 295.0 |

TABLE 1-continued

| Ingredient | Amount per capsule (mg) | | | | |
| --- | --- | --- | --- | --- | --- |
| | 0.1 mg[1] | 0.1 mg[2] | 0.5 mg[1] | 1 mg[2] | 10 mg[2] |
| Empty capsule shell | | | | | |
| Capsule shell | 48.0 | 76.0 | 48.0 | 76.0 | 76.0 |
| Total capsule weight | 198.0 | 376.0 | 198.0 | 376.0 | 371.0 |

[1]Filled in size 3 capsules;
[2]Filled in size 1 capsules

Example 3

Formulations of 4,4'-[fluoro-(1-H-1,2,4-triazol-1-yl)methylene]bisbenzonitrile (CGP47645)

The required excipients, in the respective amounts to yield the final composition as indicated in Table 2 below, and the appropriate amount of CGP47645 drug substance are weighed.

Then, approximately 50% of the amount of the filler of the premix, as indicated in Table 2 below, is filled into suitable container, the drug substance is added, followed by the remaining 50% of the amount of filler of the premix, as indicated in Table 2, to get a sandwich of drug substance between two layers of filler. Blending, sieving and again blending this mixture yields the drug substance (DS) premix.

The remaining excipients, except magnesium stearate, are mixed and sieved and transfer into a suitable container. Then the DS premix is added into container containing the sieved excipients and the mixture is blended together, sieved and mixed again. Finally, pre-sieved Magnesium stearate is added to the blend containing the DS and this mixture is blended again to yield the final blend. The final blend is filled into hard gelatin capsules.

All the excipients comply with the requirements of the applicable compendial monographs (Ph.Eur., NF). The hard gelatine capsules are packaged in HDPE bottles with aluminum induction seal equipped with child-resistant screw-cap closures.

The final dosage form is a hard gelatine capsule containing a white to yellowish powder in a pink opaque capsule, size 1 or size 3.

The following Table 2 indicates the composition of the CGP47645 hard gelatin capsule of 0.1 mg and 0.5 mg strength.

TABLE 2

| | Ingredient Capsule content | Amount per capsule (mg) (Trial No.) | | | | | |
| --- | --- | --- | --- | --- | --- | --- | --- |
| | | 0.5 mg (1) | 0.5 mg (2) | 0.5 mg (3) | 0.1 mg (4) | 0.1 mg (5) | 0.5 mg (6) |
| DS premix | CGP47645 | 0.5 | 0.5 | 0.5 | 0.1 | 0.1 | 0.5 |
| | Corn Starch | 9.5 | 13.75 | — | 14.15 | 14.15 | 13.75 |
| | Lactose monohydrate | — | — | 13.75 | — | — | — |
| | Corn Starch | 4.25 | — | 13.75 | — | — | — |
| | Cellulose, microcrystalline | 30.0 | 30.0 | 30.0 | 30.0 | 30.0 | 30.0 |
| | Lactose monohydrate | 96.0 | 96.0 | 82.25 | 96.0 | 96.0 | 96.0 |
| | Sodium starch glycolate (Type A) | 7.5 | 7.5 | 7.5 | 7.5 | 7.5 | 7.5 |
| | Magnesium Stearate | 1.5 | 1.5 | 1.5 | 1.5 | 1.5 | 1.5 |
| | Silica, colloidal anhydrous | 0.75 | 0.75 | 0.75 | 0.75 | 0.75 | 0.75 |
| | Capsule fill weight | 150.0 | 150.0 | 150.0 | 150.0 | 150.0 | 150.0 |

Blend Uniformity and Content Uniformity of the blended mixtures or capsules according to Table 2 are determined by HPLC analysis of ten samples of each composition.

The following Table 3 shows the average values of blend uniformity (BU) and content uniformity (CU) at the end of the filling step of the blended mixtures of Table 2 or the corresponding hard gelatin capsules, respectively.

TABLE 3

| | Amount per capsule (mg) (Trial No.) | | | | | |
| --- | --- | --- | --- | --- | --- | --- |
| | 0.5 mg (1) | 0.5 mg (2) | 0.5 mg (3) | 0.1 mg (4) | 0.1 mg (5) | 0.5 mg (6) |
| BU (vs. theoretical amount) | 98.7 | 95.5 | 98.7 | 100.1 | 96.6 | 99.4 |
| CU at the end of the filling step (% vs. label) | 99.8 | 99.2 | 101.2 | 103.5 | 97.0 | 102.3 |

Blend uniformity of the final blends according to Example 3 are between 95% and 101% versus the theoretical amount. Similarly the content uniformity after filling of the blend into the capsules is between 97% and 104% versus the label. No trend towards segregation was observed.

Example 4

Single ascending dose study of 4,4'-[Fluoro-(1-H-1,2,4-triazol-1-yl)methylene]bisbenzonitrile (CGP47645)

This was a randomized, double-blind, placebo- and active-controlled single ascending dose study in pre- and post-menopausal women to assess the safety and tolerability, PK and PD effects of single doses of 4,4'-[Fluoro-(1-H-1,2,4-triazol-1-yl)methylene]bisbenzonitrile (CGP47645). There were 8 cohorts of 8 post-menopausal subjects randomized 6:2, CGP47645:placebo, who received single doses of CGP47645 beginning at the dose of 0.01 mg and carried through 20 mg, which reached the limit of the toxicology exposure coverage. Patients received either 0.1 mg, 1 mg, and 10 mg drug substance containing hard gelatin capsules as described in Example 2 or appropriate matching placebo capsules. For the lowest two dosing cohorts, 0.1 mg drug containing capsules were used for reconstituting the CGP47645 oral solutions for dosing the 0.01 and 0.03 dosing strength (Cohort 1 and 2).

A minimal toxic dose (MTD) was not reached. A single cohort of 8 pre-menopausal subjects without childbearing potential (Cohort No. 9) received CGP47645 0.1 mg or placebo, randomized 6:2, and one last cohort received letrozole 2.5 mg as an internal positive control cohort for the PD measurements. Table 4 presents the PK parameters based on preliminary analysis of the concentration-time profile obtained from this study.

TABLE 4

CGP47645 Pharmacokinetics in Post- & Pre-menopausal women

| Dose (mg) | Cohort No. | Size | $C_{max}$ (ng/mL) Mean | CV (%) | $T_{max}$ (hr) Median | AUC(0-$t_{last}$) (ng*hr/mL) Mean | CV (%) | $T_{1/2}$ (days) Mean | CV (%) |
|---|---|---|---|---|---|---|---|---|---|
| 0.01 | 1 | (n = 5) | 0.2 | 21.7 | 1 | 1.4 | 53.2 | 2.3 | 127.5 |
| 0.03 | 2 | (n = 6) | 0.4 | 18.7 | 0.6 | 24.1 | 34.0 | 16.5 | 36.0 |
| 0.1 | 3 | (n = 6) | 1.8 | 13.4 | 1 | 123.1 | 10.7 | 18.2 | 10.9 |
| 0.3 | 4 | (n = 6) | 5.1 | 14.1 | 1 | 605.1 | 49.0 | 23.5 | 19.9 |
| 1 | 5 | (n = 5) | 12.8 | 22.0 | 1 | 3201.9 | 37.2 | 22.4 | 38.5 |
| 3 | 6 | (n = 6) | 38.4 | 17.0 | 1 | 10053.0 | 16.7 | 25.0 | 8.4 |
| 10 | 7 | (n = 6) | 123.8 | 26.4 | 2 | 41745.5 | 17.3 | 27.3 | 17.6 |
| 20 | 8 | (n = 6) | 269.8 | 30.9 | 2 | 76731.6 | 11.4 | 26.9 | 16.5 |
| 0.1 | 9 | (n = 6) | 1.7 | 15.1 | 1 | 116.2 | 17.1 | 23.5 | 31.0 |
| 2.5 | Letrozole | (n = 8) | 33.5 | 27.0 | 1 | 1667.7 | 40.8 | 2.9 | 40.7 |

CGP47645 exhibited dose proportional pharmacokinetics and a dose-dependent inhibition of estrone, estrone sulfate and estradiol. No differences in CGP47645 pharmacokinetics were observed between post- and pre-menopausal women. CGP47645 is rapidly absorbed with a $T_{max}$ of 0.5-2 hrs. Both $C_{max}$ & AUC increased in a dose-proportional manner. CGP47645 exhibited low inter-subject variability of 10-30% and completely unexpected long half-life in the range of 23 to 27 days.

The study showed evidence of efficacy in PD parameters with estrone suppression at least equal to letrozole already at doses of 0.1 mg and 0.3 mg. In postmenopausal women, the lowest single dose at which transient estrogen suppression was seen was 0.01 mg; and the lowest single dose at which maximal estrogen suppression was observed in post-menopausal women, using chemiluminescence or radioimmunoassay, was 0.1 mg. No inhibition of other enzymes involved in steroid hormone synthesis or metabolism was observed; in particular there were no changes in androgen levels, progesterone, aldosterone, cortisol, ACTH, or 17-keto or 17-OH steroids in 24 hour urine collections. There were no changes in bone density by DEXA after 6 months.

The invention claimed is:

1. A pharmaceutical composition, in the form of a capsule, comprising a blended mixture comprising
    (a) a therapeutically effective amount of 4,4'-[fluoro-(1-H-1,2,4-triazol-1-yl)methylene] bisbenzonitrile which amount is from about 0.01 to about 3 mg per capsule;
    (b) one or more filler;
    (c) one or more disintegrant;
    (d) one or more lubricant, and
    (e) one or more glidant.

2. A pharmaceutical composition according to claim 1, wherein said therapeutically effective amount of 4,4'-[fluoro-(1-H-1,2,4-triazol-1-yl)methylene]bisbenzonitrile is about 0.01 mg, about 0.05 mg, about 0.1 mg, about 0.3 mg, about 0.5 mg, about 1 mg, about 2 mg, or about 3 mg per capsule.

3. A pharmaceutical composition according to claim 1, wherein said filler is selected from one or more of microcrystalline cellulose; low-substituted hydroxypropyl cellulose; hydroxyethyl cellulose; hydroxypropyl methyl cellulose; sugars, sugar alcohols, starches, starch derivatives; tricalcium phosphate, calcium hydrogen phosphate, calcium sulfate, dibasic calcium phosphates, and magnesium oxide.

4. A pharmaceutical composition according to claim 1, wherein said filler is selected from one or more of microcrystalline cellulose, lactose, and maize starch.

5. A pharmaceutical composition according to claim 1, wherein said disintegrant is selected from one or more of carboxymethylcellulose calcium (CMC-Ca), carboxymethylcellulose sodium (CMC-Na), crosscarmellose sodium, Sodium Starch Glycolate, alginic acid, sodium alginate and guar gum.

6. A pharmaceutical composition according to claim 1, wherein said lubricant is selected from one or more of magnesium stearate, aluminium silicate, calcium silicate, stearic acid, cutina, PEG 4000-8000, and talc.

7. A pharmaceutical composition according to claim 1, wherein said glidant is selected from one or more of colloidal silicon dioxide, magnesium trisilicate, powdered cellulose, starch, and talc.

8. A method for preparing a pharmaceutical composition according to claim 1 comprising the steps of:

(a) sequentially adding two portions of one or more filler and one portion of the therapeutic compound 4,4'-[fluoro-(1-H-1,2,4-triazol-1-yl)methylene] bisbenzonitrile (CGP47645) in the order first portion filler, therapeutic compound, second portion filler into a suitable mixing vessel and mixing the layers of the components using a suitable mixer to produce a pre-mix,
(b) sieving the pre-mix through a sieve with a mesh size of not more than 1.0 mm, preferably a mesh size of 0.5 mm,
(c) optionally mixing the sieved pre-mix using a suitable mixer,
(d) sieving a mixture of the remaining excipients, except the lubricant, through a sieve with a mesh size of not more than 1.0 mm, preferably a mesh size of 0.5 mm,
(e) mixing the pre-mix with the mixture of the remaining excipients, except the lubricant, using a suitable mixer,
(f) sieving the resulting mixture through a sieve with a mesh size of not more than 1.0 mm,
(g) optionally mixing the sieved mixture using a suitable mixer,
(h) sieving the lubricant, through a sieve with a mesh size of not more than 1.0 mm, and subsequently adding the lubricant to the resulting mixture of step (f) or (g),
(i) mixing the resulting mixture using a suitable mixer to obtain the final blend, and
(j) filling the final blend of step (i) into capsules, optionally using a suitable capsule filling machine.

9. A method of using the pharmaceutical composition of claim 1 in the treatment of a condition or disorder associated with aromatase activity.

10. The pharmaceutical composition of claim 5 wherein said disintegrant is Sodium Starch Glycolate.

11. The pharmaceutical composition of claim 6 wherein said lubricant is magnesium stearate.

12. The pharmaceutical composition of claim 6 wherein said glidantis colloidal silicon dioxide.

13. A pharmaceutical composition according to claim 1, wherein
said filler is selected from the group consisting of microcrystalline cellulose, lactose and maize starch, and mixtures thereof,
said disintegrant is Sodium Starch Glycolate (SSG),
said lubricant is magnesium stearate, and
said glidant is colloidal silicon dioxide.

14. A pharmaceutical composition according to claim 1 wherein
said filler is employed in an amount ranging from about 80% to about 96% by weight of the capsule content,
said disintegrant is employed in an amount ranging from about 3% to about 6% by weight of the capsule content,
said lubricant is employed in an amount ranging from about 0.25% to about 5% by weight of the capsule content, and
said glidant is employed in an amount ranging from about 0.25% to about 1% by weight of the capsule content.

15. A pharmaceutical composition of claim 1 wherein said therapeutically effective amount of 4,4'-[fluoro-(1-H-1,2,4-triazol-1-yl)methylene]bisbenzonitrile is from 0.1 mg to 1.0 mg per capsule.

16. A pharmaceutical composition of claim 13 wherein said therapeutically effective amount of 4,4'-[fluoro-(1-H-1,2,4-triazol-1-yl)methylene]bisbenzonitrile is from 0.1 mg to 1.0 mg per capsule.

17. A pharmaceutical composition of claim 16 wherein said filler is a mixture of microcrystalline cellulose, lactose and maize starch.

* * * * *